US00PP27344P3

(12) United States Plant Patent
Klemm et al.

(10) Patent No.: US PP27,344 P3
(45) Date of Patent: Nov. 1, 2016

(54) ***OSTEOSPERMUM* PLANT NAMED 'KLEOE14243'**

(50) Latin Name: ***Osteospermum ecklonis* Norl.**
Varietal Denomination: KLEOE14243

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 84 days.

(21) Appl. No.: 14/545,028

(22) Filed: Mar. 18, 2015

(65) Prior Publication Data

US 2016/0278270 P1 Sep. 22, 2016

(51) Int. Cl.
*A01H 5/02* (2006.01)

(52) U.S. Cl.
USPC ..... Plt./360

(58) Field of Classification Search
USPC ..... Plt./360
See application file for complete search history.

*Primary Examiner* — June Hwu
(74) *Attorney, Agent, or Firm* — Barbara Campbell; Bethany R. Roahrig; Cochran Freund & Young, LLC

(57) ABSTRACT

A new *Osteospermum* plant particularly distinguished by yellow ray florets and a semi-upright growth habit, is disclosed.

1 Drawing Sheet

Genus and species: *Osteospermum ecklonis* Norl.
Variety denomination: 'KLEOE14243'.

BACKGROUND OF THE NEW PLANT

The present invention comprises a new and distinct variety of *Osteospermum*, botanically known as *Osteospermum ecklonis*, and hereinafter referred to by the variety name 'KLEOE14243'. 'KLEOE14243' originated from a controlled cross conducted in summer 2010 in Nairobi, Kenya between the proprietary female *Osteospermum* variety 'OE-2009-0827' (unpatented), and the proprietary male *Osteospermum* variety 'OE-2000-BA01' (unpatented).

The seeds from the cross were sown and plants were grown in a greenhouse for evaluation, where an individual plant designated 'KLEOE14243' was selected from the group of plants in April 2011. In May 2011, 'KLEOE14243' was first vegetatively propagated by terminal vegetative cuttings. 'KLEOE14243' was found to reproduce true to type in successive generations of asexual propagation via terminal tip vegetative cuttings.

SUMMARY

The following are the most outstanding and distinguishing characteristics of this new variety when grown under normal horticultural practices in Stuttgart, Germany.

1. Yellow ray florets; and
2. A semi-upright growth habit.

DESCRIPTION OF THE PHOTOGRAPH

This new *Osteospermum* plant is illustrated by the accompanying photograph which shows the plant's overall plant habit including form, foliage, and flowers. The photograph is of a four-month-old plant grown outdoors in Stuttgart, Germany in August 2012.

The colors shown are as true as can be reasonably obtained by conventional photographic procedures.

DESCRIPTION OF THE NEW VARIETY

The following detailed descriptions set forth the distinctive characteristics of 'KLEOE14243'. The data which define these characteristics were collected from asexual reproductions carried out in Stuttgart, Germany. Data was collected on five-month-old plants grown in a greenhouse in Stuttgart, Germany in March 2015 using CCC 0.1% and 0.2% for growth regulation and artificial light, SONT and LED for 16 hours in alternation. Color references are to The R.H.S. Colour Chart of The Royal Horticultural Society of London (R.H.S.), 5$^{th}$ edition (2007).

Classification:

*Family.*—Asteraceae.
*Botanical.*—*Osteospermum ecklonis.*
*Common.*—*Osteospermum*; African daisy.
*Designation.*—'KLEOE14243'.
*Parentage.*—Female parent: The proprietary female *Osteospermum* variety 'OE-2009-0827' (unpatented). Male parent: The proprietary male *Osteospermum* variety 'OE-2000-BA01' (unpatented).

Plant:

*Form and habit.*—Herbaceous perennial but usually cultivated as an annual; not frost resistant.
*Growth habit.*—Semi-upright.
*Branching habit.*—Freely branching.
*Height (from top of soil, including inflorescence).*—About 20.0 cm.
*Width (including inflorescences).*—About 30.0 cm.
*Propagation.*—Terminal tip cuttings.
*Time to produce a finished flowering plant.*—14 weeks (winter to spring).
*Time to initiate and develop roots.*—About 3 weeks.
*Root description.*—Freely rooting, light tan in color.

Leaves:
- *Arrangement.*—Alternate.
- *Shape.*—Oblanceolate.
- *Apex.*—Acute.
- *Base.*—Acute.
- *Margin.*—Medium indentation of margin/serrate.
- *Immature color.*—Upper surface: RHS 141B. Lower surface: RHS 141C.
- *Mature color.*—Upper surface: RHS 139A. Lower surface: RHS 141C.
- *Length.*—About 5.0 cm to 6.0 cm.
- *Width.*—About 2.0 cm.
- *Texture and appearance* (*upper and lower surfaces*).—Leathery with a covering of fine hairs.
- *Petioles.*—Absent.
- *Venation pattern.*—Pinnate.
- *Venation color.*—Upper surface: RHS 144A. Lower surface: RHS 141C.

Stems:
- *Total number of branches per plant* (*calculated at the base of the plant*).—About 7.
- *Length.*—Up to 14.0 cm.
- *Diameter.*—About 0.6 cm.
- *Internode length.*—Between 1.0 cm and 2.0 cm.
- *Color.*—RHS 144B.
- *Texture.*—Pubescent, a covering of fine hairs.
- *Anthocyanin.*—Absent.

Flower buds:
- *Shape.*—Ovate.
- *Length.*—About 1.0 cm to 1.5 cm.
- *Diameter.*—About 1.0 cm.
- *Color* (*at tight bud just before the ray florets unfold*).—RHS 143B.

Inflorescence:
- *Type.*—Composite, single.
- *Blooming habit.*—Spring to autumn.
- *Quantity of inflorescences per plant.*—About 30.
- *Lastingness of the inflorescences on the plant.*—About 2 weeks.
- *Fragrance.*—Absent to faint.
- *Inflorescence diameter.*—About 7.0 cm.
- *Inflorescence depth.*—About 1.5 cm.
- *Disc diameter.*—About 1.5 cm.

Disc floret:
- *Quantity per inflorescence.*—70 to 80.
- *Shape.*—Lanceolate.
- *Tube color.*—Closed: RHS 145A. Mature: RHS 1C.
- *Length.*—About 0.5 cm.
- *Diameter* (*at apex*).—About 0.1 cm.
- *Apex.*—Obtuse.
- *Apex color.*—RHS 1C.
- *Base.*—Acute.
- *Base color.*—RHS 157D.
- *Margin.*—Entire.

Ray floret:
- *Quantity per inflorescence.*—About 20.
- *Shape.*—Oblanceolate.
- *Color.*—Upper surface: RHS 9A and RHS 6A at the base. Lower surface: RHS 12A.
- *Length.*—3.0 cm to 3.5 cm.
- *Width.*—0.9 cm.
- *Apex.*—Obtuse.
- *Base.*—Acute.
- *Margin.*—Entire.
- *Texture* (*both upper and lower surfaces*).—Smooth.

Peduncle:
- *Length.*—Up to 8.0 cm.
- *Diameter.*—About 0.2 cm.
- *Texture.*—Pubescent, a covering of fine hairs.
- *Color.*—RHS 144B.

Phyllaries:
- *Texture.*—Pubescent, a covering of fine hairs.
- *Color.*—RHS 143A.
- *Arrangement.*—Single.
- *Observed quantity per flower.*—About 20.
- *Shape.*—Lanceolate.
- *Color.*—Upper surface: RHS 143A. Lower surface: RHS 143B.
- *Length.*—About 1.0 cm.
- *Width.*—0.1 cm to 0.2 cm.
- *Apex.*—Acute.
- *Base.*—Obtuse.
- *Margin.*—Entire.
- *Texture.*—Upper surface: Pubescent, a covering of fine hairs. Lower surface: Shiny.

Reproductive organs:
- *Androecium.*—Location: On the disc floret only. Stamens: Quantity: Numerous. Shape: Filamentous. Filament length: About 0.5 cm. Filament diameter: Less than 0.005 cm. Anther: Shape: Lanceolate. Color: RHS 203A. Length: About 0.3 cm. Diameter: Less than 0.05 cm. Pollen: Color: RHS 14A. Amount: Moderate.
- *Gynoecium.*—Location: On the base of the ray florets, reduced on disc florets. Pistils: Number: About 20 fully developed on ray florets. Length: 0.3 cm. Diameter: Less than 0.05 cm. Stigma: Color: RHS 6C. Shape: Split in two parts at the end. Length: About 0.1 cm. Diameter: Less than 0.05 cm. Style: Color: RHS 4D. Length: 0.3.cm. Diameter: Less than 0.05 cm.

Fruit and seed set: None observed.

Disease and pest/insect resistance: No disease and pest/insect resistance observed.

COMPARISON WITH PARENTAL LINES AND KNOWN VARIETY

'KLEOE14243' is distinguished from its parents, the female parent 'OE-2009-0827' (unpatented) and the male parent, 'OE-2000-BA-01' (unpatented), as described in Table 1.

TABLE 1

Comparison with Parental Lines

| Characteristic | 'KLEOE14243' | Female Parent 'OE-2009-0827' | Male Parent 'OE-2000-BA01' |
|---|---|---|---|
| Ray floret color | Yellow | Yellow with pink ring at the base | Yellow |
| Peduncle length | Moderately long | Moderately long | Very long |

'KLEOE14243' is most similar to the commercial *Osteospermum* variety 'KLEOE11187' (U.S. Plant Pat. No. 24,034). Differences between the varieties are described in Table 2.

TABLE 2

| Comparison with Similar Variety | | |
|---|---|---|
| Characteristic | 'KLEOE14243' | 'KLEOE11187' |
| Ray floret, width of ring at the base | Absent to very narrow | Medium |
| Ray floret, shape of apex | Obtuse | Acute |

We claim:

1. A new and distinct variety of *Osteospermum* plant designated 'KLEOE14243' as illustrated and described herein.

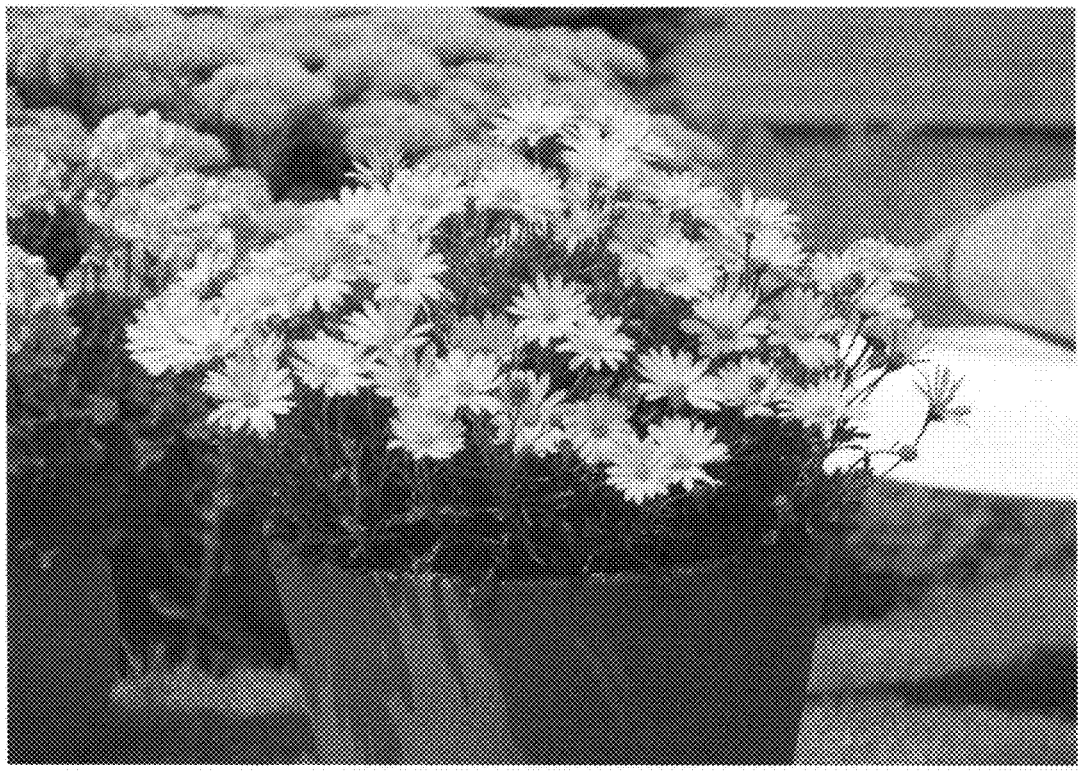

* * * * *